(12) United States Patent
Pierce et al.

(10) Patent No.: US 7,716,030 B2
(45) Date of Patent: May 11, 2010

(54) TARGET LIGAND GENERATION

(75) Inventors: Albert Pierce, Cambridge, MA (US); Guy Bemis, Arlington, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 1100 days.

(21) Appl. No.: 10/790,507

(22) Filed: Mar. 1, 2004

(65) Prior Publication Data

US 2004/0236555 A1 Nov. 25, 2004

Related U.S. Application Data

(60) Provisional application No. 60/450,723, filed on Feb. 28, 2003.

(51) Int. Cl.
*G06G 7/58* (2006.01)
*G01N 33/48* (2006.01)

(52) U.S. Cl. .............................. 703/11; 702/19; 702/20; 702/21; 703/12

(58) Field of Classification Search ........................ None
See application file for complete search history.

(56) References Cited

OTHER PUBLICATIONS

Bemis et al. "The Properties of Known Drugs. 1. Molecular Frameworks" *J. Med. Chem.* 39:2887-2893 (1996).
Böhm et al. "The computer program LUDI: A new method for the de novo design of enzyme inhibitors" *J. Comput.-Aided Mol. Des.* 6:61-78 (1992).
Brooks et al. "CHARMM: A Program for Macromolecular Energy, Minimization, and Dynamics Calculations" *J. Comput. Chem.* 4:187-217 (1983).
Charifson et al. "Consensus Scoring: A Method for Obtaining Improved Hit Rates from Docking Databases of Three-Dimensional Structures into Proteins" *J. Med. Chem.* 42:5100-5109 (1999).
Eldridge et al. "Empirical scoring functions: I. The development of a fast empirical scoring function to estimate the binding affinity of ligands in receptor complexes" *J. Comput.-Aided Mol. Des.* 11:425-445 (1997).
Ewing et al. "Critical Evaluation of Search Algorithms for Automated Molecular Docking and Database Screening" *J. Comput. Chem.* 18(9):1175-1189 (1997).
Flower "SERF: A program for accessible surface area calculations" *J. Mol. Graphics Model.* 15:238-244 (1998).
Gasteiger et al. "Automatic Generation of 3D-Atomic Coordinates for Organic Molecules" *Tetrahed Comp. Meth.* 3:537-547 (1990).
Gasteiger et al. "Chemical Information in 3D Space" *J. Chem. Inf. Comput. Sci.* 36:1030-1037 (1996).
Gehlhaar et al. "Molecular recognition of the inhibitor AG-1343 by HIV-1 protease: conformationally flexible docking by evolutionary programming" *Chem. Bio.* 2:317-324 (1995).
Guex et al. "SWISS-MODEL and the Swiss-PdbViewer: An environment for comparative protein modeling" *Electrophoresis* 18:2714-2723 (1997).
Halgren "Merck Molecular Force Field. I. Basis, Form, Scope, Parameterization, and Performance of MMFF94" *J. Comput. Chem.* 17:490-519 (1996).
Halgren "Merck Molecular Force Field. III. Molecular Geometries and Vibrational Frequencies for MMFF94" *J. Comput. Chem.* 17:553-586 (1996).
Halgren "Merck Molecular Force Filed. II. MMFF94 van der Waals and Electrostatic Parameters for Intermolecular Interactions" *J. Comput. Chem.* 17:520-552 (1996).
Ho et al. "SPLICE: A program to assemble partial query solutions from three-dimensional database searches into novel ligands" *J. of Computer-Aided Mol. Desig.* 7:623-647 (1993).
Holm et al. "Protein Structure Comparison by Alignment of Distance Matrices" *Mol. Biol.* 233:123-138 (1993).
Honig et al. "Classical Electrostatics in Biology and Chemistry" *Science* 268:1144-1149 (1995).
Jones et al. "Development and Validation of a Genetic Algorithm for Flexible Docking" *J. Mol. Biol.* 267(3):727-748 (1997).
Jorgensen et al. "Development and Testing of the OPLS All-Atom Force Field on Conformational Energetics and Properties of Organic Liquids" *J. Am. Chem. Soc.* 118:11225 (1996).
Klabunde et al. "Drug Design Strategies for Targeting G-Protein-Coupled Receptors" *Chem. Bio. Chem.* 3:928-944 (2002).
Kleywegt et al. "Detecting Folding Motifs and Similarities in Protein Structures" *Meth. Enzymol.* 277:525-545 (1997).
Kollman "Free Energy Calculations: Applications to Chemical and Biochemical Phenomena" *Chem. Rev.* 93:2395-2417 (1993).
Lehtonen et al. "Finding Local Structural Similarities Among Families of Unrelated Protein Structures: A Generic Non-Linear Alignment Algorithm" *Proteins* 34:341-355 (1999).
Lemmen et al. "Computational methods for the structural alignment of molecules" *J. Comp-Aided Molec. Des.* 14:215-232 (2000).
Lybrand "Ligand-protein docking and rational drug design" *Current Opin. in Structural Biol.* 5:224-228 (1995).
Madej et al. "Threading a Database of Protein Cores" *Proteins* 23:356-369 (1995).
Meng et al. "Automated Docking with Grid-Based Energy Evaluation" *J. Comp. Chem.* 13:505-524 (1992).
Miller et al. "FLOG: A system to select 'quasi-flexible' ligands complementary to a receptor of known three dimensional structure" *J. Computer-Aided Mol. Des.* 8:153-174 (1994).
Murray et al. "Empirical scoring functions. II. The testing of an empirical scoring function for the prediction of ligand-receptor binding affinities and the use of Bayesian regression to improve the quality of the model" *J. Comput-Aided Mol. Design* 12:503-519 (1998).
Pierce et al. "Kinase Inhibitors and the Case for CH•••O Hydrogen Bonds in Protein-Ligand Binding" *Proteins* 49:567-576 (2002).
Russell "Detection of Protein Three-dimensional Side-chain Patterns: New Examples of Convergent Evolution" *J. Mol. Biol.* 279:1211-1227 (1998).
Schmitt et al. "A New Method to Detect Related Function Among Proteins Independent of Sequence and Fold Homology" *J. Mol. Biol.* 323:387-406 (2002).

(Continued)

*Primary Examiner*—Shubo (Joe) Zhou
(74) *Attorney, Agent, or Firm*—Michael J. DiVerdi

(57) ABSTRACT

Methods of identifying potential ligands for macromolecular targets are disclosed herein. The methods comprise providing models of three dimensional structural information for ligands or a ligand:macromolecule complex, mapping spatial relationships between the models, and identifying one or more pairs of matching bonds. Databases and apparatuses are also provided.

37 Claims, 8 Drawing Sheets

OTHER PUBLICATIONS

Shindyalov et al. "Protein structure alignment by incremental combinatorial extension (CE) of the optimal path" *Protein Engin.* 11(9):739-747 (1998).

Shoichet et al. "Molecular Docking Using Shape Descriptors" *J. Comput. Chem.* 13:380-397 (1992).

Stouch et al. "A Simple Method for the Representation, Quantification, and Comparison of the Volumes and Shapes of Chemical Compounds" *J. Chem. Inf. Comput. Sci.* 26:4-12 (1986).

Walters et al. "Prediction of 'drug-likeness'" *Adv. Drug Deliv. Rev.* 54(3):255-271 (2002).

Walters et al. "Recognizing molecules with drug-like properties" *Curr. Opin. Chem. Biol.* 3(4):384-387 (1999).

Walters et al. "Virtual screening—an overview" *Drug. Disc. Today* 3:160-178 (1998).

Weininger et al. "SMILES. 2. Algorithm for Generation of Unique SMILES Notation" *J. Chem. Inf. Comput. Sci.* 29:97-101 (1989).

Yamada et al. "Structure-Function Analysis of Vitamin D and VDR Model" *Curr. Pharm. Des.* 6:733-748 (2000).

TARGET LIGAND GENERATION

CROSS-REFERENCE TO RELATED APPLICATIONS

This application claims the benefit of priority of U.S. Ser. No. 60/450,723, filed Feb. 28, 2003, the contents of which are hereby incorporated by reference in its entirety.

BACKGROUND

Our understanding of the relationship between the molecular structure of macromolecules and their biological function is constantly increasing. Advances in molecular biology have made the processes of isolating and characterizing macromolecules more routine. These advances have been accompanied by advances in techniques to solve, analyze, and predict the three-dimensional structures of macromolecules using X-ray crystallography, NMR spectroscopy, cryoelectron microscopy, and computational means (Drenth, J., Principles of Protein X-ray Crystallography 1999, Wiley, New York; Siegal et al., Curr Opin Chem Biol. 3(5):530-6, 1999; Kuhlbrandt and Williams, Curr Opin Chem Biol. 3(5):537-43, 1999; Burley et al., Nat Genet. 23(2):151-7, 1999; Uson and Sheldrick, Curr Opin Struct Biol. 2(5):643-8, 1999; Skolnick and Fetrow, Trends Biotechnol. 18(1):34-9, 2000; Gohlke and Klebe, Angew Chem Int Ed. 41:2644-2676, 2002). Also, the massive amounts of information produced by genome-sequencing projects is adding to the pool of molecules available for structural comparison.

This abundance of data can be applied to the design of ligands, provided that efficient methods of manipulating the data are developed and refined.

SUMMARY

The invention is based, in part, on the discovery that computational methods can be used to generate models of potential ligands for macromolecular targets. In particular, structural models of a plurality of ligands (including ligands derived from ligand:macromolecule complexes) are fragmented and recombined with each other in silico. Ligands for recombination are not selected randomly, but rather, are selected on the basis of various user-specified criteria, such as the degree of relatedness between the ligands, or the degree of relatedness between the macromolecules bound by the ligands (e.g., structural homology between receptors of each ligand). These steps help maximize the use of known structural information, and lead to new structures that are compatible with the target macromolecule of interest.

In one aspect, the invention features a method, the method including:

(1) providing a set of models, wherein each model includes three-dimensional structural information for a ligand or a ligand:macromolecule complex; wherein each model is related to the other models of the set by a homologous structural feature;

(2) mapping spatial relationships between the models such that the models are superimposed with respect to the homologous structural feature;

(3) identifying one or more pairs of matching bonds between ligands of the set, wherein the matching bonds comprise a bond of a first ligand (B1) and a bond of a second ligand (B2) that are superimposed in step (2) such that (i) an atom at each end of the bond (B1) is within 1.8 angstrom of an atom at each end of the bond (B2), (ii) the bond (B1) and the corresponding bond (B2) are of the same bond order, and (iii) the bond (B1) and the corresponding bond (B2) are related by an angle of 30° or less;

(4) selecting a plurality of subsets of atoms and/or bonds from each ligand; wherein each subset includes a bond and/or, an atom connected to the matching bond; and (5) generating output ligands, each output ligand including atoms and/or bonds of a first subset and atoms and/or bonds of a second subset, wherein the first subset and the second subset include atoms and/or bonds derived from opposite ends of the matching bond.

In various embodiments, the models provided in step (1) are selected, prior to the providing, on the basis of any number of criteria including, but not limited to, the presence of the homologous structural feature with respect to which the models are superimposed in step (2), or the presence of another homologous structural feature. These homologous features, for either step, can include homology between the target macromolecules, homology between the ligands, shared features of a substructure of the target macromolecule (e.g., peptide backbone) or homology in a substructure of the ligand (e.g., a framework or pharmacophore of the ligand).

The output ligands can include all atoms represented in the ligands of step (1).

In one embodiment, the matching bonds are bonds that are superimposed in step (2) such that the sum of the distances between the atoms at each end of each bond is less than 2 angstroms and the absolute value of the difference between the distances is less than 0.4 angstroms.

Each model of the set can include a ligand:macromolecule complex. One or more models of the set can consist of a ligand structure (e.g., a ligand structure independent of a macromolecule).

The macromolecule can be, for example a protein (e.g., a protein kinase, a G-protein coupled receptor, an immunoglobulin superfamily protein, a protease, or a zinc-finger containing protein) or a nucleic acid (e.g., DNA, RNA).

Each model of the set can include an identical macromolecule (e.g., bound to different ligands).

The structural information can be derived from a physical observation (e.g., x-ray crystallography or NMR). The structural information can also include information derived by a computational inference (e.g., by modeling the structure of a ligand in a target macromolecule using computational means).

The ligand can be, for example, a small molecule, e.g., a molecule of 100-5000 atomic mass units (a.m.u.), or 300-1000 a.m.u., or 200-800 a.m.u.

The homologous feature can be structural homology between the ligands, e.g., structural homology including homology between a framework of the ligands, or between pharmacophore models of the ligands.

In one embodiment, the macromolecule is a protein, and the homologous feature includes structural homology between the proteins, e.g., amino acid homology of 25%, 40%, or greater, e.g., a shared polypeptide fold.

Each set of models can include two models. Alternatively, the set of models can include at least three, four, five, or six models.

The method can further include, for example, the steps of:

(6) comparing output ligands of step (5) to the ligands of step (1); and (7) storing output ligands that are not identical to the ligands used in a previous iteration of steps (2)-(5) (e.g., in a suitable machine-readable medium).

The method can further include the step of generating one or more output models, wherein each output model comprises the stored ligand docked into a target macromolecule.

The method can further include refining the output models, e.g., by performing energy minimization computations.

The output models can be evaluated, and, optionally, a score can be assigned to each output model based on the evaluating.

The method can also include a step of synthesizing or procuring a composition that includes a compound corresponding to an output ligand from a subset of output models, wherein the subset includes output models having a score in a preselected range. The composition (e.g., the composition that includes the compound) can be evaluated in physical experiments, e.g., for binding to a target macromolecule, or for an ability to modulate activity of a target macromolecule.

Steps 2-7 of the method can be repeated, and the models superimposed in step (2) can include the stored output ligands of step (7). The repeating can be automatic. The repeating can stop, e.g., when each ligand of step (7) is identical to a ligand provided in the previous step (2) of the repetition (e.g., the step (2) immediately prior to the final step (7)).

The structural information provided in step (1) of the method can include information for hydrogen atoms of the ligands and the bonds to hydrogen atoms. Alternatively, the structural information can exclude information for hydrogen atoms of the ligands.

The ligands can include a macrocyclic moiety, and two or more matching bonds can be identified within the macrocycle of each ligand.

In another aspect, the invention features a database of output ligands, the database including a plurality of records, each record including, e.g., information representing the arrangement of atoms in the output ligand (e.g., the 2-D chemical structure showing the identity of the atoms in the output ligand and the connectivity between the atoms), wherein the output ligands are generated by the following steps:

(1) providing a set of models, wherein each model includes three-dimensional structural information for a ligand or a ligand:macromolecule complex; wherein each model is related to the other models of the set by a homologous structural feature;

(2) mapping spatial relationships between the models such that the models are superimposed with respect to the homologous structural feature;

(3) identifying one or more pairs of matching bonds between ligands of the set, wherein the matching bonds comprise a bond of a first ligand (B1) and a bond of a second ligand (B2) that are superimposed in step (2) such that (i) an atom at each end of the bond (B1) is within 1.8 angstrom of an atom at each end of the bond (B2), (ii) the bond (B1) and the corresponding bond (B2) are of the same bond order, and (iii) the bond (B11) and the corresponding bond (B2) are related by an angle of 30° or less;

(4) selecting a plurality of subsets of atoms and/or bonds from each ligand; wherein each subset comprises a bond and/or, an atom connected to the matching bond;

(5) generating output ligands, each output ligand comprising atoms and/or bonds of a first subset and atoms and/or bonds of a second subset, wherein the first subset and the second subset comprise atoms and/or bonds derived from opposite ends of the matching bond;

(6) comparing output ligands to the ligands of step (1);

(7) storing output ligands that are not identical to the ligands of step (1) (e.g., in a machine-readable medium);

(8) repeating steps (2)-(7), wherein the models superimposed in step (2) comprise the stored output ligands of step (7); wherein the repeating stops, e.g., when each output ligand of step (7) is identical to a ligand provided in step (2) of the previous repetition.

The database can further include, for example, the 3-D structural positions of atoms of the output ligands.

In various embodiments, the models provided in step (1) are selected, prior to the providing, on the basis of any number of criteria including, but not limited to, the presence of the homologous structural feature with respect to which the models are superimposed in step (2), or the presence of another homologous structural feature, e.g., homology between the target molecules, homology between the ligands, shared features of a substructure of the target molecule (e.g., peptide backbone) or in a substructure of the ligand (e.g., a framework or pharmacophore of the ligand).

The output ligands can include all atoms represented in the ligands of step (1).

The matching bonds can be bonds that are superimposed in step (2) such that the sum of the distances between the atoms at each end of each bond is less than 2 angstroms and the absolute value of the difference between the distances is less than 0.4 angstroms.

Each model of the set can include a ligand:macromolecule complex, e.g., each model of the set can include an identical macromolecule (e.g., bound to different ligands). The macromolecule can be, for example a protein (e.g., a protein kinase, a G-protein coupled receptor, an immunoglobulin superfamily protein, a protease, or a zinc-finger containing protein) or a nucleic acid (e.g., DNA, RNA).

In some embodiments, one or more models of the set consists of structural information for a ligand.

The structural information can be derived from a physical observation (e.g., X-ray crystallography or NMR) and/or can include information derived by a computational inference (e.g., by modeling the structure of a ligand in a target macromolecule using computational means).

The ligand can be, for example, a small molecule, e.g., a molecule of 100-5000 atomic mass units (a.m.u.), or 300-1000 a.m.u., or 200-800 a.m.u. The homologous feature can be structural homology between the ligands, e.g., structural homology including homology between the framework of the ligands, or between pharmacophore models of the ligands.

In one embodiment, the macromolecule is a protein, and the homologous feature includes structural homology between the proteins. The homology between proteins include amino acid homology of 25%, 40%, or greater, and/or a shared polypeptide fold.

The set of models can include two, three, four, five, six, or more models.

The steps can further include, for example, the steps of:

(6) comparing output ligands of step (5) to the ligands of step (1); and (7) storing (e.g., in a suitable machine-readable medium) output ligands that are not identical to the ligands used in a previous iteration of steps (2)-(5).

The steps can further include the step of generating one or more output models, wherein each output model comprises the stored output ligand docked into a target macromolecule, and/or refining the output models, e.g., by performing energy minimization computations, and, optionally, evaluating the models and assigning a score to each output model based on the evaluating.

The structural information provided in step (1) can include information for hydrogen atoms of the ligands and the bonds to hydrogen atoms. Alternatively, the structural information can exclude information for hydrogen atoms of the ligands. The ligands can include a macrocyclic moiety, and two or more matching bonds can be identified within the macrocycle of each ligand.

In another aspect, the invention features an apparatus that includes:

(a) a memory that stores executable instructions; and
(b) a processor that executes the instructions to:
  (1) provide a set of models, wherein each model includes three-dimensional structural information for a ligand or a ligand:macromolecule complex;
    wherein each model is related to the other models of the set by a homologous structural feature;
  (2) map spatial relationships between the models such that the models are superimposed with respect to the homologous structural feature;
  (3) identify one or more pairs of matching bonds between ligands of the set, wherein the matching bonds include a bond of a first ligand (B1) and a bond of a second ligand (B2) that are superimposed in step (2) such that
    (i) an atom at each end of the bond (B1) is within 1.8 angstrom of an atom at each end of the bond (B2), (ii) the bond (B1) and the corresponding bond (B2) are of the same bond order, and (iii) the bond (B1) and the corresponding bond (B2) are related by an angle of 30° or less;
  (4) select a plurality of subsets of atoms and/or bonds from each ligand;
    wherein each subset includes a bond and/or, an atom connected to the matching bond;
  (5) generate output ligands, each output ligand including atoms and/or bonds of a first subset and atoms and/or bonds of a second subset, wherein the first subset and the second subset include atoms and/or bonds derived from opposite ends of the matching bond;
  (6) compare output ligands to the ligands of step (1);
  (7) store output ligands that are not identical to the ligands of step (1);
  (8) repeat steps (2)-(7), wherein the models superimposed in step (2) comprise the stored output ligands of step (7); wherein the repeating stops, e.g., when each output ligand of step (7) is identical to a ligand provided in step (2) of the previous repetition. The instructions can execute other steps described herein, and the steps can include other features described herein.

In another aspect, the invention features an article including machine-readable media that stores executable instructions, the instructions causing a machine to:

(1) provide a set of models, wherein each model includes three-dimensional structural information for a ligand or a ligand:macromolecule complex; wherein each model is related to the other models of the set by a homologous structural feature;
(2) map spatial relationships between the models such that the models are superimposed with respect to the homologous structural feature;
(3) identify one or more pairs of matching bonds between ligands of the set, wherein the matching bonds include a bond of a first ligand (B1) and a bond of a second ligand (B2) that are superimposed in step (2) such that
  (i) an atom at each end of the bond (B1) is within 1.8 angstrom of an atom at each end of the bond (B2), (ii) the bond (B1) and the corresponding bond (B2) are of the same bond order, and (iii) the bond (B1) and the corresponding bond (B2) are related by an angle of 30° or less;
(4) select a plurality of subsets of atoms and/or bonds from each ligand;
  wherein each subset includes a bond and/or, an atom connected to the matching bond;
(5) generate output ligands, each output ligand including atoms and/or bonds of a first subset and atoms and/or bonds of a second subset, wherein the first subset and the second subset include atoms and/or bonds derived from opposite ends of the matching bond;
(6) compare output ligands to the ligands of step (1);
(7) store output ligands that are not identical to the ligands of step (1);
(8) repeat steps (2)-(7), wherein the models superimposed in step (2) include models the stored output ligands of step (7); wherein the repeating stops, e.g., when each output ligand of step (7) is identical to a ligand provided in the step (2) of the previous repetition. The instructions can execute other steps described herein, and the steps can include other features described herein.

In another aspect, the invention features an article including machine-readable media that stores executable instructions, the instructions causing a machine to:

(1) map spatial relationships between two or more models of ligands of a set such that the models are superimposed, wherein each model includes three-dimensional structural information for a ligand;
(2) identify one or more pairs of matching bonds between ligands of the set, wherein the matching bonds include a bond of a first ligand (B1) and a bond of a second ligand (B2) that are superimposed in step (2) such that (i) an atom at each end of the bond (B1) is within 1.8 angstrom of an atom at each end of the bond (B2), (ii) the bond (B1) and the corresponding bond (B2) are of the same bond order, and (iii) the bond (B1) and the corresponding bond (B2) are related by an angle of 30° or less;
(3) select a plurality of subsets of atoms and/or bonds from each ligand;
  wherein each subset includes a bond and/or, an atom connected to the matching bond;
(4) generate output ligands, each output ligand comprising atoms and/or bonds of a first subset and atoms and/or bonds of a second subset, wherein the first subset and the second subset include atoms and/or bonds derived from opposite ends of the matching bond. The instructions can execute other steps described herein, and the steps can include other features described herein.

As used herein, the terms "ligand", "macromolecule", and "model" refer to in silico representations of physical molecules, except where otherwise noted.

The term "mapping spatial relationships" refers to computational analysis of the position of one or more atoms in a virtual, three-dimensional representation of a molecule.

The term "compatible", as used herein, refers a favorable interaction between, e.g., a ligand and a target macromolecule, including an interaction in which the ligand binds and/or modulates the activity of the target macromolecule.

The details of one or more embodiments of the invention are set forth in the accompanying drawings and the description below. Other features, objects, and advantages of the invention will be apparent from the description and drawings, and from the claims. All cited patents, patent applications, and references (including references to public sequence database entries) are incorporated by reference in their entireties for all purposes. U.S. Ser. No. 60/447,827 (filed Feb. 14, 2003) and U.S. Ser. No. 60/450,723 (filed Feb. 28, 2003) are incorporated by reference in their entireties for all purposes.

DESCRIPTION OF DRAWINGS

Like reference symbols in the various drawings indicate like elements.

DETAILED DESCRIPTION

The present invention provides systems, methods, and computer instructions for generating new molecular ligands for preselected target macromolecules. The invention also provides a database containing these new ligands. These methods can be applied to the generation of modulatory ligands (e.g., inhibitors, activators) for macromolecules (e.g., biopolymers such as proteins or nucleic acids).

The development of these methods was undertaken to automate the process of generating new ligands based on physicochemical structural information, hence ensuring that a maximal number of structurally reasonable pairings of ligand fragments would be generated. According to the invention, novel computer-assisted steps integrate molecular recombination and three-dimensional structural information to produce ligands. The molecular recombination is not random, but rather, implements limitations based on spatial overlap between either the ligand or target molecules. This feature favors the production of ligand molecules that are compatible with the target of interest. Furthermore, the 'offspring' of the original ligands can be added to the pool of initial compounds for recombination and generation of a new set of ligands. In this manner, a small number of initial structures can be used to create a large set of potential ligands. These ligands do not simply combine the scaffold of one known ligand with the sidechain of another and are not limited to hybrids of two different scaffolds. With only two iterations of this molecular ligand breeding, many of the new molecules generated bear little resemblance to any of the initial ligand structures, combining scaffold and sidechain elements from two and more lead compounds.

Generation of New Ligands

Figure 1:
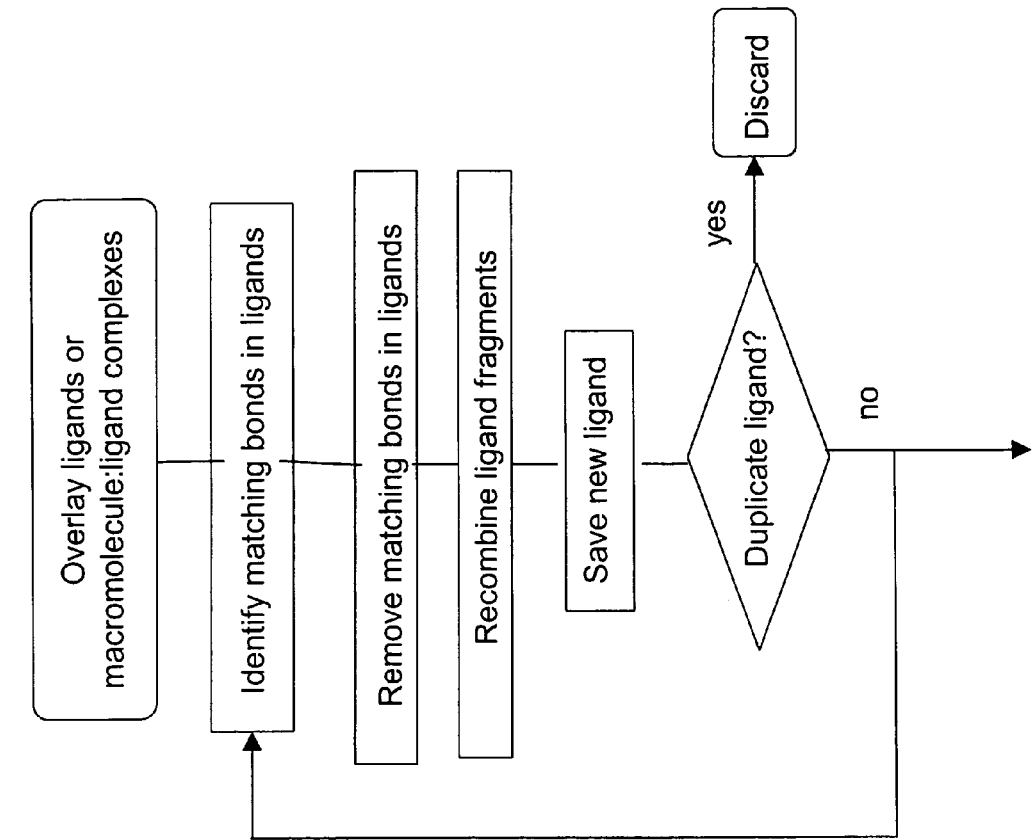
FIG. 1 is a flowchart diagram of exemplary steps of a molecular ligand breeding method.

Referring to the flow diagram in FIG. 1, the first step in the application of molecular ligand breeding is the overlay of three-dimensional molecular structures. The choice of structural models with which to initiate the molecular ligand breeding process critically affects the results of the process. The user can specify a homologous structural feature which must be shared between the ligands and/or the target molecules (e.g., macromolecules, e.g., protein receptors). Thus, the choice of molecular structures to overlay will depend on information that is available for the starting ligands and target molecules, and the choice of the user in determining a preferred homologous structural feature. In one example, the user recombines two inhibitors for an enzyme. The 3-D structure for the enzyme in a complex with each ligand is known. The user may overlay the atoms in one particular region of the enzyme (e.g., a region with catalytic activity). A subset of atoms in the enzyme (e.g., the backbone or $C^\alpha$ atoms, atoms defining a binding pocket or active site, etc.) can be superimposed. Preferably, atoms from an inflexible portion of a macromolecule that form direct interactions with ligands are superimposed. An advantage of selecting structures for breeding based on a shared structural feature of the target molecules (e.g., a shared structural feature other than a putative ligand pharmacophore) is that the method is less reliant on ligand-based homology, thus reducing the degree of bias towards particular ligand elements.

In other examples, the user recombines ligands from two enzymes that share a desired degree of structural homology (rather than being ligands of a single enzyme), or from ligands that share structural homology, or from ligands that have been virtually "docked" into a target molecule (rather than solved by physical observation). The methods described herein are such that multiple combinations of molecules (sets of ligand:macromolecule complexes, sets of ligands alone, etc.) can be used as starting ligands for the recombination process, so long as they possess a degree of relatedness that can allow implementation of the ligand breeding steps described below. Initiation of ligand breeding with models related in this manner maximizes both the use of known structural information and the potential compatibility of new ligands with the target of interest. Additional information with respect to ligand and macromolecule structures and methods of performing overlaying is provided in the sections below.

Figure 2:
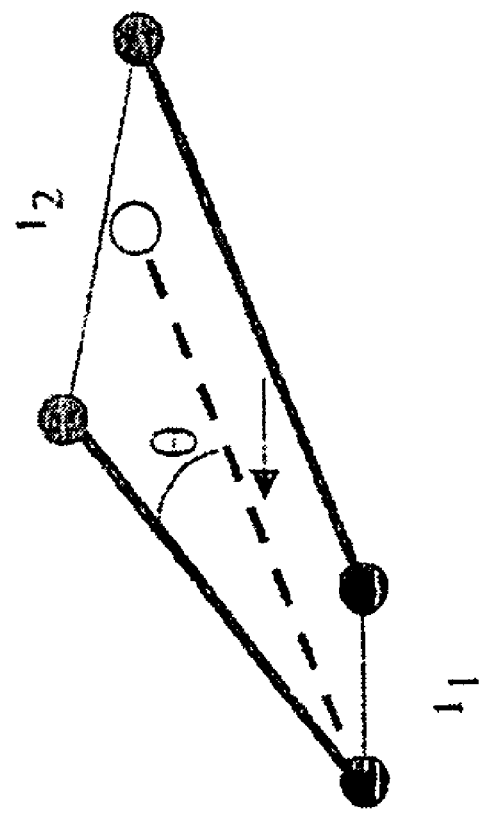
FIG. 2 is a diagram depicting the geometric requirements for determining matching bonds in the process of molecular ligand breeding. Dark circles represent atoms, thick lines represent bonds. Thin lines show $r_1$ and $r_2$, the distances between the atoms at each end of the bond. The dashed line shows the right-hand bond translated left so that the angle between the two bonds, $\theta$, can be calculated.
Figure 3:
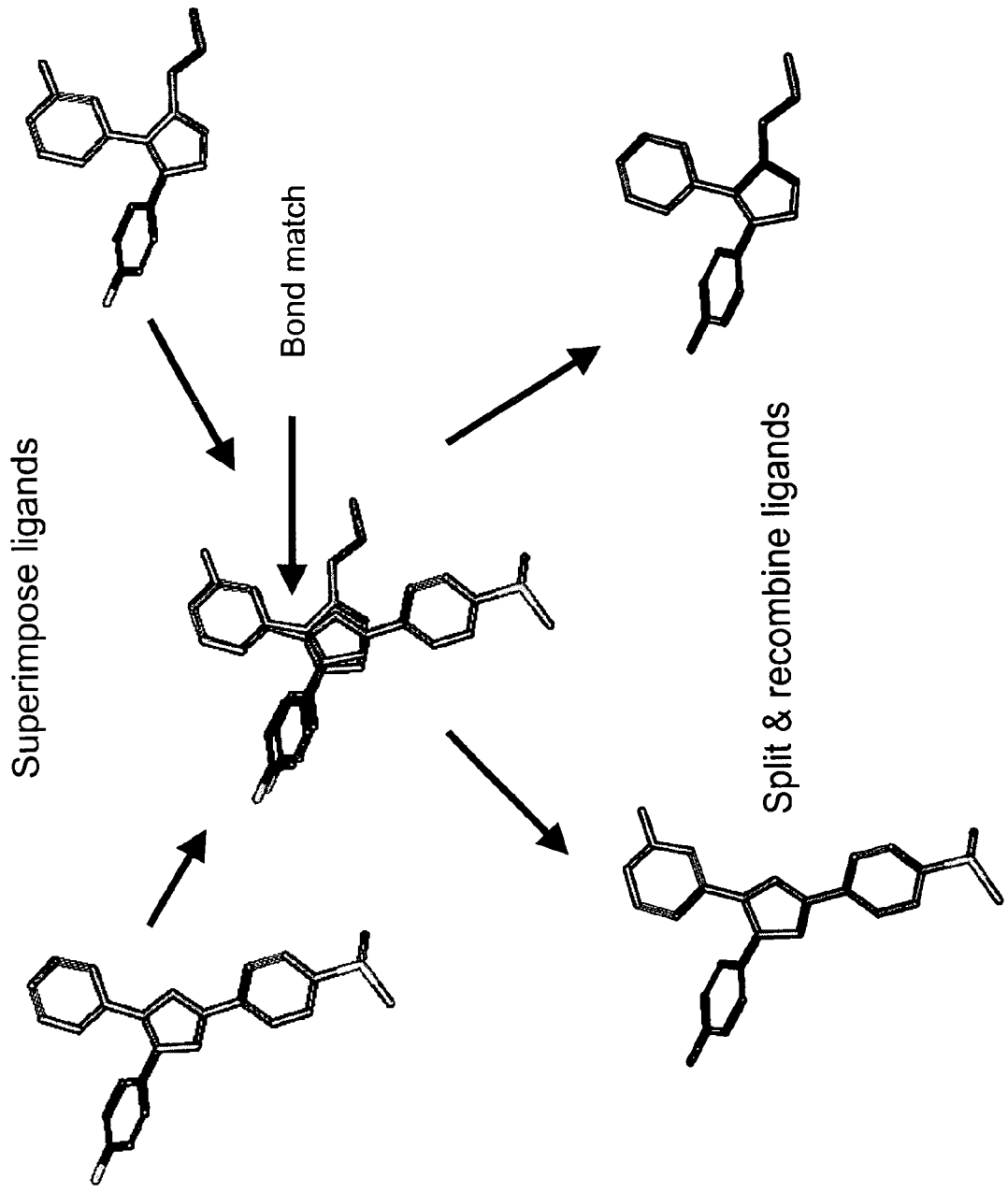
FIG. 3 is depiction of two starting ligands, the superposition of the ligands, and two output ligands generated by splitting and recombining the starting ligands.

Once the appropriate molecules are aligned and the ligands are in a common reference frame, the ligands are stored in an electronic file format suitable for structural data, e.g., an SD file. Ligands can be stored without explicit hydrogen atoms, or, for increased output, with explicit hydrogen atoms. Next, the files containing the 3-D molecules are read and stored as bonds (with orders and connected atoms) and atoms (with 3-D coordinates). Pairs of ligands are considered to find all matching bonds between the two molecules. A pair of bonds is considered to be matching if three conditions are met. First, the two bonds must be of the same order (i.e., a single bond and a double bond cannot be considered a match). This limitation maintains the hybridization/geometry of the bonded atoms in the new molecule. Second, bonds must be superimposable such that certain geometric requirements are met (FIG. 2). In one embodiment, the atoms at each end of the bond must overlap within about 1.8 angstroms of each other, or preferably, one angstrom. And, the angle between the bond vectors of the two bonds (FIG. 2, θ) must be no greater than 30°, or preferably, no greater than 15°. These geometric requirements are depicted graphically in FIG. 2. In an alternate embodiment, the requirements for bond matching can be determined as follows. The matching bonds can be superimposed such that the sum of the distances between the atoms at each end of each bond (FIG. 2, $r_1+r_2$) is less than 2 angstroms and the absolute value of the difference between the distances (e.g., $|r_2-r_1|$) is less than 0.4 angstroms. FIG. 3 is a 3-D illustration of two ligands, the superpositioning of the two ligands containing a bond match, and two output ligands generated by ligand breeding. The margins of error in the bond matching requirements are reasonable relative to the limits of crystal structure resolution, protein flexibility and the accuracy of protein alignments. They have also been chosen to ensure that the molecules output by the ligand breeding process do not have excessively distorted geometries. In some implementations of ligand breeding, matching bond pairs can be identified within cyclic moieties, with recombination occurring between the matching bonds.

After performing this process of identifying matching bonds, copies of each original ligand are stored. The matching bond is removed, thereby generating partial molecules. This process is repeated for the other ligand(s) and the partial molecules are joined. The partial molecules from opposite ends of a matching bond can be joined to give new ligands. The resulting set of molecules is generated such that duplicates do not reappear in the set (see below).

Figure 4:
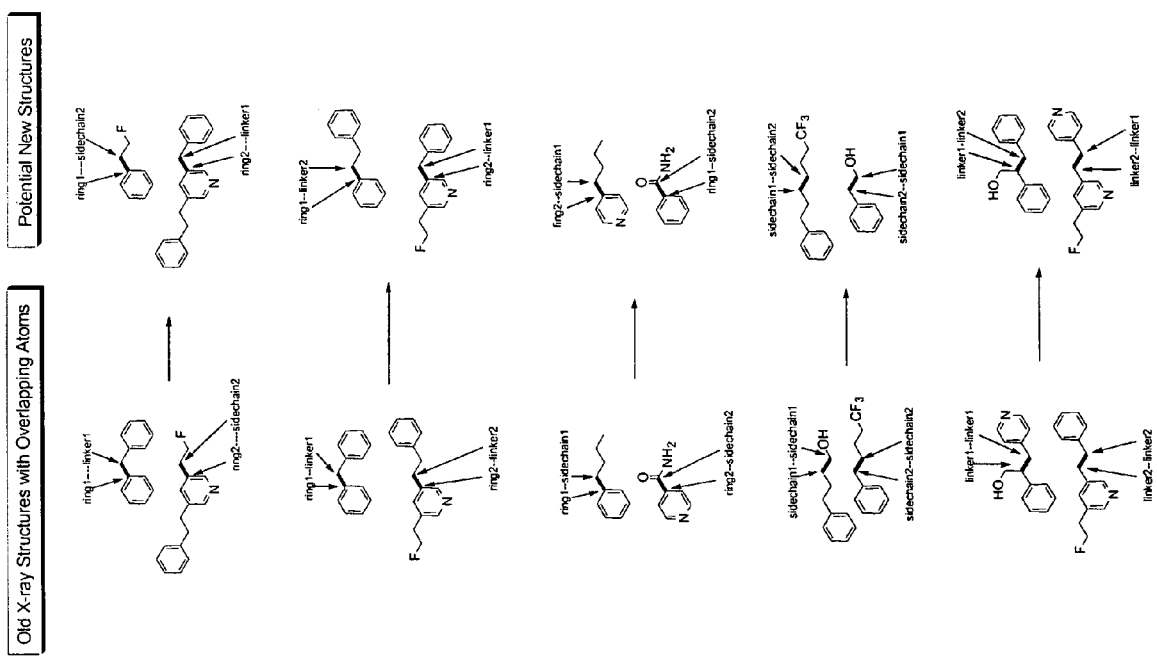
FIG. 4 is a depiction of sets of hypothetical starting ligands and potential new structures that can be derived from those ligands when ligand breeding is applied. Overlapping bonds are shown in bold.

For each pair of matching bonds among two molecules, two new molecules are generated, as depicted in FIGS. 3 and 4. In one example in which two initial molecules share a single matching bond, the molecules are split into two 'halves' at the matching bond. One new molecule consists of the first 'half' of molecule one and the second 'half' of molecule two. The other new molecule is made up of the second 'half' of molecule one and the first 'half' of molecule two. All of the atoms in the new molecules have essentially the same atom types, positions and bonds as the corresponding atoms in the parent compounds, except for the two atoms that make up the matching bond. These two atoms are identical except for their Cartesian coordinates, which are the average of the Cartesian coordinates of the corresponding atom in both parent molecules. This averaging gives the new bond between the two 'halves' of the molecule a more appropriate bond length and a bond vector closer to the bond vectors of the parent compounds. As each new molecule is generated, its structure is compared to the structures of all the initial and previously generated molecules. The structures can be compared using a format appropriate for such comparisions of molecules, e.g., using canonical SMILES (Weininger et al., *J Chem Inf Comput Sci.* 29:97-101, 1989). If it is not a duplicate, the molecule is output into a file that stores results.

An example of computer instructions to perform the steps above is provided by breed.py, shown in the Appendix. These instructions use the OEChem Python toolkit (OpenEye Scientific Software, Inc.) and the Phython programming language (Python Software Foundation python.org. The instructions can be compatible with, for example, version 1.0 or version 1.1 beta of OEChem. One of skill in the art can adapt the instructions to be compatible with alternate version of OEChem.

Briefly, the OEChem Python toolkit is used to read and store the 3-D molecules as described above. The instructions direct the steps of identifying matching bonds and removing bonds and atoms, and the instructions direct placement of an appropriate bond between the two halves. Then OEChem is used to convert the molecule to the canonical SMILES string format. OEChem can also convert the molecule to other formats, such as MDL mol format. Other software packages that can be used to implement the ligand breeding steps in place of OEChem include the Daylight SMILES Toolkit with the Daylight Depict Toolkit (Daylight Chemical Information Systems, Inc., Mission Viejo, Calif.). Alternatively, various steps can be instructed using a suitable programming language, including those known in the art, e.g., C++, FORTRAN, Perl, or Python computer programming languages alone by adding instructions to read, write, and convert molecules into a readable format appropriate for molecular structures, e.g., canonical SMILES.

The new molecules in the file that stores results can be viewed in many packages of molecular visualization software, minimized, scored or otherwise processed as potential lead compounds (see below). The ligands in this file can also be reprocessed by the ligand breeding steps (e.g., those steps instructed by breed.py, in the Appendix). If the file of initial compounds is concatenated with the file of new compounds, the methods of the invention can be applied to the concatenated file to generate additional new ligands, either with user intervention at any step in the process or without intervention by the user, thus resulting in an output set of ligands. When all possible recombinations have been made iteratively, and ligand breeding produces only duplicate structures, the ligand breeding can stop.

Macromolecules

The molecular ligand breeding methods described herein can be applied to the generation of new ligands for any target macromolecule of interest. Target macromolecules can include, for example, polypeptides such as protein kinases, nuclear hormone receptors, ion channels, G-protein coupled receptors, phosphatases, and proteases, and nucleic acids such as DNA, RNA, ribozymes, etc. Three-dimensional structural information is available for numerous macromolecules and macromolecule:ligand complexes. This information can be based on x-ray structural coordinates of the macromolecules and macromolecule:ligand complexes. Information can also be derived from NMR and neutron diffraction methods.

The term "structure coordinates" refers to three-dimensional atomic coordinates derived from mathematical equations related to the experimentally measured intensities obtained upon diffraction of a mono-or polychromatic beam of X-rays by the atoms (scattering centers) of a macromolecule or macromolecule:ligand complex in crystal form. The diffraction data can be used to calculate an electron density map of the repeating unit of the crystal. The electron density maps can be used to establish the positions of the individual atoms within the unit cell of the crystal. Alternatively, computer programs such as XPLOR can be used to establish and refine the positions of individual atoms.

Crystals of the macromolecule or macromolecule:ligand complex can be produced or grown by a number of techniques including batch crystallization, vapor diffusion (either by sitting drop or hanging drop), soaking, and by microdialysis. Seeding of the crystals in some instances is required to obtain X-ray quality crystals. Standard micro and/or macro seeding of crystals can therefore be used. Once a crystal of the present invention is produced, X-ray diffraction data can be collected. The example below used standard cryogenic conditions for such X-ray diffraction data collection though alternative methods can also be used. For example, diffraction data can be collected by using X-rays produced in a conventional source (such as a sealed tube or rotating anode) or using a synchrotron source. Methods of X-ray data collection include, but are not limited to, precession photography, oscillation photography and diffractometer data collection. Data can be processed using packages including, for example, DENZO and SCALPACK (Z. Otwinowski and W. Minor) and the like.

Coordinates for regions of macromolecular structures can also be obtained from databases such as the Protein Data Bank maintained by Brookhaven National Laboratory, Upton, N.Y. (Berman, et al., *Nuc Acids Res.* 28(1):235-242, 2000), and the Nucleic Acid Database Project (NDB) (Berman et al., *Biophys. J.*, 63:751-759, 1992).

The methods described here need not only utilize information derived from macromolecule:ligand complexes whose structure has been determined by a physical observation. Information can be derived from 3-D structures of a macromolecule in which a ligand has been "docked" using computational structure-based drug design (SBDD) methods (see section on Docking below). The ligand may be a ligand known to bind the macromolecule, or it may be a ligand that was determined to be appropriate for the macromolecule by other means. For example, a ligand having modulatory activity when complexed with a related macromolecule can be appropriate. Or a ligand having structural similarity with a known ligand can be appropriate. Structurally relevant features include, for example, side chains that comprise part of a pharmacophore, or a substructural framework. Combination of docked structures with the experimentally determined structures greatly increases the number of new ligands generated by this method, with the user aware of potential false positives based on improperly docked structures. Methods of performing docking are described below.

The methods described herein can also involve the superpositioning of 3-D structures of related macromolecules, each optionally containing a bound ligand, rather than simply superpositioning of identical macromolecules containing distinct ligands. Related macromolecules include polypeptide members of a particular gene family, polypeptides having topologically similar binding sites, polypeptides having at least 20%-30% homology within the domain of interest.

A number of criteria can be used to determine whether a set of macromolecules are related enough to each other to use for the alignment and ligand breeding steps of the method. Three-dimensional relatedness for polypeptides is often classified in terms of molecular folds, or protein domains. A protein fold or domain typically has a characteristic secondary structure and topological connections (Murzin et al., *J. Mol. Biol.* 247: 536-540, 1995). The Structural Comparison of Proteins (SCOP) database is a useful resource for identification of proteins within a given family or superfamily, or having a related fold or other structural feature that would allow superpositioning with a molecule, or complex, of interest (Murzin et al., supra). Another method of comparing proteins to determine homology involves the database PROSITE (http://expasy.hcuge.ch), containing signatures or sequence patterns (or motifs) or profiles of protein families or domains. Proteins containing a sequence that comprises a "signature" or sequence pattern or profile derived for, and identified in PROSITE as relating to a second protein, would be considered homologous such that breeding would be appropriate between ligands of the two proteins.

Also, the degree of ligand overlap required for implementation of ligand breeding necessarily requires relatedness between macromolecules, in instances where macromolecules are used as a point of reference for superpositioning.

Alternatively, a ligand having a 3-D structure that is known or can be modelled can serve as a starting ligand for the ligand breeding methods, with or without a target macromolecule (see section on ligands below).

Ligands

Starting ligands for the ligand breeding methods are not limited to those having any particular size or chemical composition. The ligands can be small molecules, e.g., organic compounds of between 100-5000 a.m.u., or alternatively between 300-1000 a.m.u., or between 200-800 a.m.u. In one aspect, the ligand used for ligand breeding can include 1-5 heteroaryl or heterocyclic rings. The ligand can be a non-peptide.

Explicit hydrogen atoms may or may not be included in the initial structures for processing. Inclusion of hydrogen atoms can increase the number of acyclic bonds available for matching, and consequently increase the yield of new compound recombinations.

For ligand breeding based on recombination between acyclic bonds, it is clear that some classes of inhibitors will be more prolific than others. For example, macrocycles and steroidal compounds have few acyclic bonds and therefore may generate few new ligands. However, modified implementations of ligand recombination can be applied to these classes of molecules. For instance, macrocycle processing could be handled by searching for two matching bond pairs at different points in the macrocycle. The intervening stretch of molecule can then be exchanged to generate two new compounds.

As mentioned above, ligands can serve as starting molecules for ligand breeding in the absence of an associated macromolecular structure. These ligands can have a 3-D structure that is known, or that can be modeled computationally. Sources of 2-D structural information for starting ligands include the Comprehensive Medicinal Chemistry (CMC) database, the MACCS-II Drug Data Report (MDDR), the Available Chemicals Database (ACD) (all from MDL, Inc., San Leandro, Calif.), the World Drug Index (WDI) (Derwent Information, London, UK). "Virtual" structural libraries can also be used.

Output ligands generating by the ligand breeding methods can be compared to molecules, e.g., from the databases above.

In some implementations, ligand breeding methods will employ steps in which structural models are related by features shared amongst ligand structures. The shared feature may be a framework, substructure, or pharmacophore shared between the ligands. Frameworks, substructures, and pharmacophores can be identified as follows.

Frameworks. Small molecules can be deconstructed into substructures consisting of ring, linker, framework, and sidechain atoms (Bemis and Murcko, *J Med Chem.* 39:2887-2893, 1996). A molecular framework is the union of ring systems and linkers in a molecule, and in various embodiments, a framework can be defined to include additional atoms, and/or to reflect particular atomic properties such as topological torsions.

The use of framework substructures for identification of related ligands has a number of advantages. The shape descriptor methods used to identify frameworks are computationally simple to execute and can be applied to compare large numbers of structures, thus providing a large pool of possible matches. Furthermore, ligand frameworks frequently contain key protein-recognition elements (e.g., hydrogen-bonding atoms and hydrophobic moieties) that determine ligand binding orientation in protein/ligand complexes. For example, two out of three hydrogen bonds typically formed between the adenosine moiety in ATP and the hinge region of protein kinases are formed with atoms in the ATP framework. Frameworks are also easy to manipulate computationally. Thus, reduction of molecular databases to frameworks and selection of appropriate frameworks is easily automated.

A framework can be identified as described in Bemis and Murcko (*J Med Chem*, supra). Briefly, side chain atoms of a query molecule are identified and removed until each atom is bonded to at least two other atoms. Side chain atoms are defined as atoms that are bonded to only one other atom. The remaining atoms are the framework atoms. Ring or cyclic atoms can further be identified by a depth-first search (Cormen et al. *Intro to Algorithms*, MIT Press, Cambridge, 1990, pp.447-485). Ring atoms can include heteroatoms such as nitrogen, oxygen, or sulfur atoms. Non ring atoms are linker atoms. In some embodiments, carbonyl groups are considered to be part of the framework.

Common Substructures. Ligands can be modeled based on information for a ligand having a substructure identical to that of the query ligand. A common substructure sufficient for breeding between ligands can contain, e.g., at least a few, e.g., 4-6 atoms in common. A common substructure may include atoms that are part of a framework (as defined in the section above). A common substructure may also include atoms that are part of a pharmacophore (as defined below).

Commercially available software packages can be used to perform maximum common substructure searches. For example, OEChem Python Toolkit and Theory Manual (Version: 1.0 Beta, Chapter 17.3, Oct. 25, 2002, OpenEye Scientific Software, Inc.) contains computer code that can be used to perform maximum common substructure searches (Chapter 17.3, Oct. 25, 2002 version).

Pharmacophores. A pharmacophore is a spatial arrangement of the structural elements of a molecule that confer biochemical or pharmacological effects on that molecule. The pharmacophore of a ligand can be identified, e.g., by the following process. First, ligand atoms that are involved in hydrogen-bonding (H-bonding) to the target macromolecule are identified. For particular classes of macromolecules, these hydrogen bonds form within a distinct region of the target. For example, H-bonds form between the ligands and the "hinge" region of protein kinases. Computer programs known in the art can be used to identify H-bonds. For example, WebLab ViewerPro (Version 4.0 ©, Molecular Simulations, Inc.) and DeepView Swiss-PDB Viewer (expasy.org/spdbv/; Guex, and Peitsch. *Electrophor.* 18:2714-2723, 1997) can be used to identify these atoms. Hydrogen-bond interactions between CH and O atoms can be identified manually. See, e.g., Pierce et al., *Proteins* 49:576-576, 2002, for geometric parameters useful in identifying CH to O hydrogen bonding interactions.

Typically, the next step in pharmacophore identification is to generate a model of the ligands in which all ring systems containing hydrogen-bonding ligand atoms, all hydrogen-bonding ligand atoms contained in acyclic protions of the molecule, and all acyclic atoms needed to connect the fragments above into one contiguous molecular entity are fused.

Superpositioning

To perform molecular ligand breeding, three dimensional representations of molecules are created, regions to be superimposed are determined, and then superimposed to enable identification of bond matches between ligands. Programs useful for creating 3-D representations of molecules from 2-D information include CONCORD (Tripos Inc., St. Louis, Mo.) and CORINA (Gasteiger et al., *Tetrahed Comp Meth.* 3: 537-547, 1990; Gasteiger et al., *J. Chem. Inf. Comput. Sci.* 36:1030-1037, 1996).

A variety of methods are available for computational superpositioning of macromolecular structures. Superpositioning (e.g., superimposing, overlaying, structural alignment) of macromolecules can be performed by overlaying subsets of atoms related by sequence homology (Guex and Peitsch, *Electrophoresis* 18:2714-2723, 1997), or shared fold (Holm, and Sander, *Mol. Biol.* 233:123-138, 1993), or by overlaying the sidechains (Russell, R. B., *J. Mol. Biol.* 279: 1211-1227, 1998), or functional groups (Schmitt et al., *J. Mol. Biol.* 323:387-406; 2002) arranged similarly between the two structures. For example, superposition of molecules containing a shared fold can be performed with algorithms that use three-dimensional coordinates to calculate $C^\alpha$-$C^\alpha$ distances between amino acid residues, such as DALI (Holm and Sander, supra).

In some implementations, ligands with a shared activity may be overlaid directly. A number of algorithms have been developed which consider rigid-body, semiflexible, and flexible superpositioning of small molecules (reviewed in Lemmen and Lengaur, *J Comp-Aided Molec Des.* 14:215-232, 2000). In some cases, this superpositioning of ligands can place macromolecules in the same reference frame. Tools to overlay ligand structures include MOE (Chemical Computing Group, Inc.), FlexS (cartan.gmd.de/flexs) and Medchem Explorer (Accelrys Inc., San Diego, Calif.).

Resources for identifying atoms to be superimposed, and for performing structural alignment of macromolecules include Combinatorial Extension (CE; Shindyalov and Boume, *Protein Engin.*, 11(9):739-747, 1998), VAST (Madej et al., *Proteins* 23:356-369, 1995); and DEJAVU (Kleywegt and Jones, *Meth Enzymol.* 277:525-545, 1997); MOE (Chemical Computing Group, Inc.); Swiss Pdb Viewer (Guex and Peitsch, *Electrophoresis* 18:2714-2723, 1997); and WebLab ViewerPro (Accelrys Inc., San Diego, Calif.).

Once atoms to be superimposed have been identified, programs that allow the user to specify these atoms and superimpose the structures can be implemented. Examples of such programs include MOE (Chemical Computing Group, Inc.) and ProFit (UK HGMP Resource Centre).

Docking/Refining/Evaluating

New output ligands generated by the methods described herein can be virtually placed, or "docked", into the binding site of the target macromolecule of interest and evaluated for compatibility with the target. Docking can also be used to generate macromolecule:ligand complexes prior to ligand breeding.

Computational methods can produce binding orientations for ligands within a site on a target macromolecule having a known structure and can evaluate the energetic compatibility of the ligands based on criteria such as lipophilic interactions, hydrogen bonding, repulsion between atoms, and intramolecular strain.

Docking algorithms that use rigid body minimization, flexible ligand sidechains with rigid ligand and target, or flexible ligand and target, may be used. Accounting for the flexibility/rotatability of bonds can ensure more complete sampling of binding interactions. Docking programs which can be used include DOCK (Meng, et al., *J. Comp. Chem.* 13: 505-524, 1992; Ewing and Kuntz, *Prot Engin.* 18: 1175-1189, 1993), Autodock (Molecular Graphics Laboratory), FlexX (Tripos, Inc., St. Louis, Mo.), Gold (Jones et al., *J. Mol. Biol.* 267(3): 727-48, 1997), FlexiDock (Tripos, Inc.) and Genetics-Algorithm based programs such as GAMBLER (Charifson et al., *J Med Chem.* 42:5100-5109, 1999).

Scoring functions can be used to evaluate new ligands generated by ligand breeding, or to evaluate macromolecule:

ligand models to be used as starting complexes for ligand breeding. Scoring functions include DOCK energy score (Meng et al., *J. Comp. Chem.* 13: 505-524, 1992; Ewing and Kuntz, *J. Comput. Chem.* 18:1175-1189, 1997), DOCK contact score (Shoichet et al., *J. Comput. Chem.* 13:380-397, 1992), DOCK chemical score, ChemScore (Murray et al., *J. Comput.-Aided Mol. Des.* 12:503-19, 1998; Eldridge et al., *J. Comput.-Aided Mol. Des.* 11:425-45, 1997), Piecewise Linear Potential (PLP; Gehlhaar et al., *Chem. Bio.* 2:317-324, 1995), Bohm (Bohm, H.-J., *J. Comput.-Aided Mol. Des.* 6:61-78, 1992), FLOG (Miller et al., *J. Comput.-Aided Mol. Des.* 8:153-174, 1994), Merck Molecular Force Field non-bond energy (MFF; Halgren, *J. Comput. Chem.* 17:553-586, 1996; Halgren, *J. Comput. Chem.* 17:520-552, 1996; Halgren, *J. Comput. Chem.* 17:490-519, 1996), Buried Lipophilic Surface Area (Flower, *J. Mol. Graphics Modell.* 15:238-244, 1998), Poisson-Boltzman (Honig and Nicholls, Science 268: 1144-9, 1995), the OPLS all-atom force field (Jorgensen et al., *J Am Chem Soc.* 118:11225-1123, 19966), and Volume Overlap (Stouch and Jurs, *J. Chem. Inf. Comput. Sci.* 26:4-12, 1986).

Techniques for docking and evaluating ligands within a 3-D structure of a macromolecule include the use of functions such as the AMBER force field (Kollman, *Chem Rev.* 2395-2417, 1993), and CHARMm (Brooks et al., *J Comput Chem.* 4:187-217, 1983). Monte Carlo and/or multiple copy simultaneous search techniques sample multiple orientations of a ligand in a binding pocket and can incorporate ligand flexibility (Lybrand, *Curr Op Struct Biol.* 5:224-228, 1995).

Tools for implementation of ligand refinement and scoring include ICM (Molsoft L.L.C., La Jolla, Calif.) and QUANTA (Accelrys Inc., San Diego, Calif.).

Other tools can be used to filter the new ligands based on likely in vitro activity versus the target of interest (see below). Tools have also been developed to predict the drug-likeness of compounds, their solubility, oral bioavailability, stability, toxicity, etc. Any of these can be used to rank compounds based on a given set of properties. The remaining compounds can be visually inspected for synthetic accessibility before selections for further studies are made.

Evaluating "Drug-likeness"

The "drug-likeness" of derivative ligands can be evaluated to help determine the potential usefulness of the ligand as a drug. "Drug-like" properties include the degree of oral bioavailability, water solubility, and molecular size. A number of algorithms can be applied to predict the drug-likeness of molecules (reviewed in Walters and Murcko, *Adv Drug Deliv Rev.* 54(3):255-71, 2002; Walters et al., *Curr Opin Chem Biol.* 3(4):384-7, 1999). For example, the Rapid Elimination of Swill program (REOS) eliminates molecules according to both the druggability of particular functional groups and to "rule of 5" criteria, which relate absorption of the molecule to its size, octanol-water coefficient (ClogP), the number of hydrogen-bond donors, and the number of hydrogen-bond acceptors present (Walters et al., *Drug Disc Today* 3:160-178, 1998).

Computer Systems

The ligand breeding methods of the invention can be implemented in digital electronic circuitry, or in computer hardware, firmware, software, or in combinations thereof. Computer assistance allows powerful manipulations of chemical structural data and permits automation. Furthermore, computer assistance makes possible the simultaneous comparision and recombination of multiple molecules. According to an embodiment of the invention, an apparatus (e.g., a computer), can contain computer instructions and systems that effect molecular ligand breeding. The instructions and systems can can be implemented in a computer program product tangibly embodied in a machine-readable storage device for execution by a programmable processor; and method actions can be performed by a programmable processor executing the instructions to perform molecular ligand breeding by operating on input data and generating output.

The steps of the ligand breeding methods, which can include both steps implemented by commercially available software packages, and steps implemented by instructions to perform the breeding function (e.g., breed.py) can be integrated using instructions provided with a scripting language (e.g., Perl™, Python™), or a compiled language (e.g., C, Fortran).

The methods and systems of the invention can be implemented advantageously in one or more computer programs that are executable on a programmable system including at least one programmable processor coupled to receive data and instructions from, and to transmit data and instructions to, a data storage system, at least one input device, and at least one output device. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including, by way of example, semiconductor memory devices, such as EPROM, EEPROM, and flash memory devices; magnetic disks such as, internal hard disks and removable disks; magneto-optical disks; and CD_ROM disks. Any of the foregoing can be supplemented by, or incorporated in, ASICs (application-specific integrated circuits).

Figure 5:
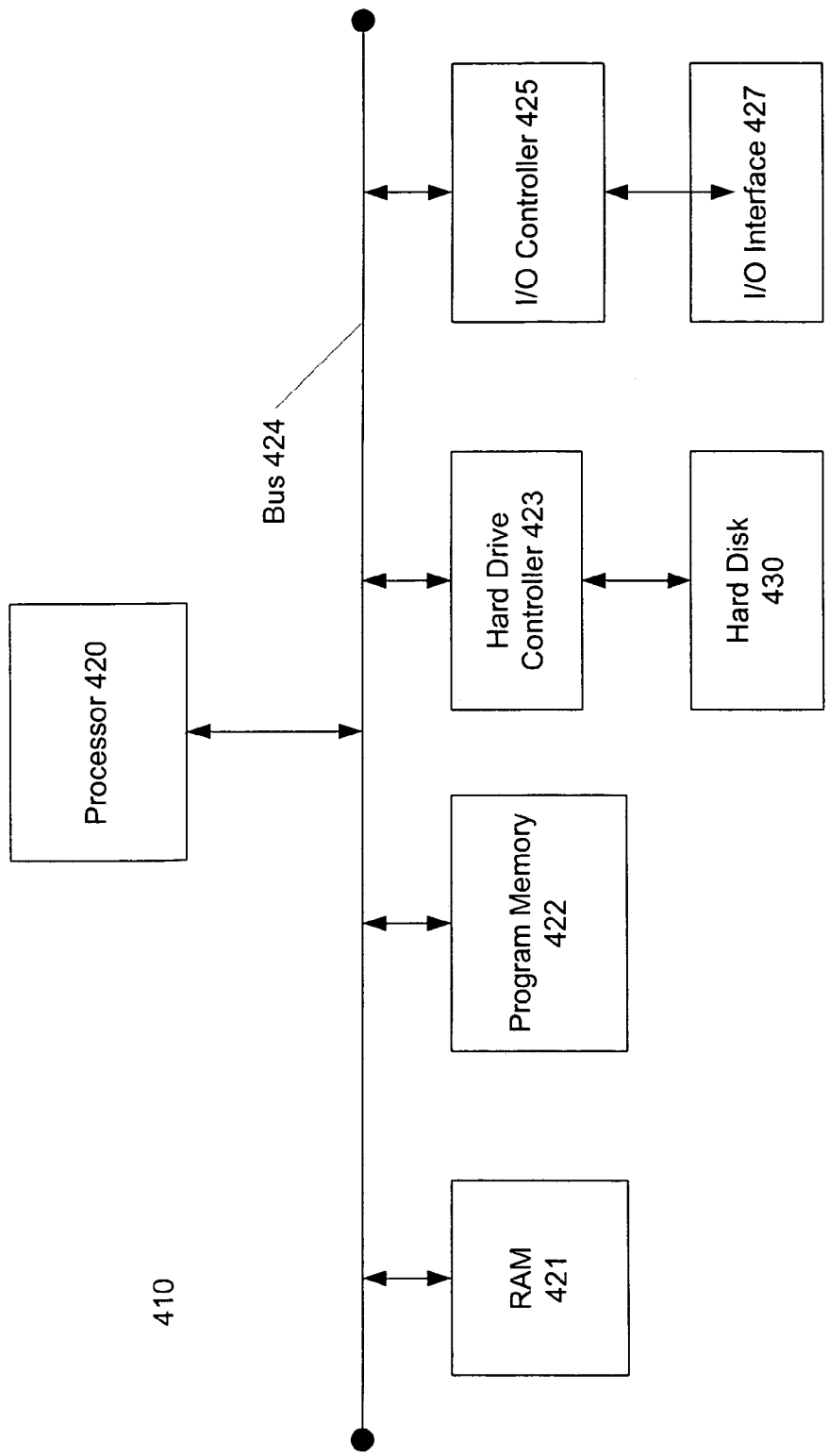
FIG. 5 is a block diagram of a computer system on which the ligand breeding method(s) can be implemented.

An example of one such type of computer is shown in FIG. 5, which shows a block diagram of a programmable processing system (system) 410 suitable for implementing or performing the apparatus or methods of the invention. The system 410 includes a processor 420, a random access memory (RAM) 421, a program memory 422 (for example, a writable read-only memory (ROM) such as a flash ROM), a hard drive controller 423, and an input/output (I/O) controller 424 coupled by a processor (CPU) bus 425. The system 410 can be preprogrammed, in ROM, for example, or it can be programmed (and reprogrammed) by loading a program from another source (for example, from a floppy disk, a CD-ROM, or another computer).

The hard drive controller 423 is coupled to a hard disk 430 suitable for storing executable computer programs, including programs embodying the present invention, and data including storage. The I/O controller 424 is coupled by means of an I/O bus 426 to an I/O interface 427, that can include one or more of the following: a monitor, a mouse, a keyboard or other input device. The I/O interface 427 receives and transmits data in analog or digital form over communication links such as a serial link, local area network, wireless link, and parallel link. One non-limiting example of an execution environment includes computers running Windows NT 4.0 (Microsoft) or Linux operating systems or operating systems compatible with the tools and methods described herein. Browsers can be Microsoft Internet Explorer version 4.0 or greater or Netscape Navigator or Communicator version 4.0 or greater. Computers for databases and administration servers can include Linux with a 90 MHz Pentium (Intel) processor or equivalent using 256 MB memory and 9 GB SCSI drive. Computer Node Hosts can include Windows NT 4.0 with a 400 MHz Pentium II (Intel) processor or equivalent using 128 MB memory and 5 GB SCSI drive. In one embodiment, implementation of the steps of ligand breeding (e.g., the steps instructed by breed.py) is performed using a Linux operating system with a 90 MHz Pentium processor with 16 MB of RAM and a 500 MB hard drive.

Compound Procurement

Chemical compounds having the structure of the output ligand, or library of output ligands (i.e., potential inhibitor, antagonist, agonist) that result from the ligand breeding process can be obtained from commercial sources or can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

In one aspect the compounds are organic small molecules, that is, compounds having molecular weight less than 1,000 amu, alternatively between 350-750 amu. In other aspects, the compounds are: (i) those that are non-peptidic; (ii) those having between 1 and 5, inclusive, heterocyclyl, or heteroaryl ring groups, which may bear further substituents; (iii) those in their respective pharmaceutically acceptable salt forms; or (iv) those that are peptidic.

The term "heterocyclyl" refers to a nonaromatic 3-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3,1-6, or 1-9 heteroatoms of N, O, or S if monocyclic, bicyclic, or tricyclic, respectively), wherein 0, 1, 2 or 3 atoms of each ring can be substituted by a substituent.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3,1-6, or 1-9 heteroatoms of N, O, or S if monocyclic, bicyclic, or tricyclic, respectively), wherein 0, 1, 2, 3, or 4 atoms of each ring can be substituted by a substituent.

The term "substituents" refers to a group "substituted" on an alkyl, cycloalkyl, aryl, heterocyclyl, or heteroaryl group at any atom of that group. Suitable substituents include, without limitation, alkyl, alkenyl, alkynyl, alkoxy, halo, hydroxy, cyano, nitro, amino, $SO_3H$, perfluoroalkyl, perfluoroalkoxy, methylenedioxy, ethylenedioxy, carboxyl, oxo, thioxo, imino (alkyl, aryl, aralkyl), S(O)nalkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), unsubstituted aryl, unsubstituted heteroaryl, unsubstituted heterocyclyl, and unsubstituted cycloalkyl. In one aspect, the substituents on a group are independently any one single, or any subset of the aforementioned substituents.

Combinations of substituents and variables in compounds (that is, chemical compounds, distinguished from virtual 3-D representations or computer representations of output ligands identified by the processes delineated herein) envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., transport, storage, assaying, therapeutic administration to a subject).

Pharmaceutically acceptable salts of the compounds herein include those derived from pharmaceutically acceptable inorganic and organic acids and bases. Examples of suitable acid salts include acetate, adipate, alginate, aspartate, benzoate, benzenesulfonate, bisulfate, butyrate, citrate, digluconate, ethanesulfonate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, pectinate, persulfatephosphate, picrate, pivalate, propionate, salicylate, succinate, sulfate, tartrate, thiocyanate, tosylate and undecanoate.

Compositions containing a compound corresponding to an output ligand generated by a method described herein may contain isomeric forms of the output ligand and/or other products of the process by which the composition was prepared.

Evaluating Compound Biological Activity

The compound can then be assayed to determine its biological function. A plethora of in vitro and in vivo screening assays and protocols for a variety of targets are well known in the art and too numerous to mention in detail. Examples include assays to measure and assess the ability of the compound to inhibit or activate a particular target. For example, enzyme targets (e.g., kinases, HIV protease) can be assayed by methods detect an activity of the enzyme (e.g., phosphorylation of a substrate, proteolysis of a substrate) and/or of enzyme-mediated pathway (e.g., stimulation of cell division by a kinase mediated pathway, HIV protease-dependent infectivity). Binding assays can be used to detect binding of the compound to the target, or a change in the binding of the target to a substrate in the presence of the compound (e.g., competition assays). Methods to detect the ability of a compound to modulate a target can be direct or indirect, and the choice of assay can be determined by the target macromolecule. For example, assays that measure localization of a target macromolecule (e.g., a transcription factor that changes localization upon activation), modification of a target molecule (e.g., phosphorylation, acetylation), modification of a substrate of a target molecule (e.g., phosphorylation of a kinase substrate, activation of transcription of a nucleic acid by a transcription factor) can be used to assess the activity of a compound on the target macromolecule.

The compound modeled and/or selected by the aforementioned processes can be assayed by any number of methods. The compounds can be used in assays, including radiolabelled, antibody detection and fluorometric. The assay can be a cell-based assay, a cell-free assay, or an in vivo assay. The compound is contacted with a sample (e.g., cell, or cell lysate) and a measurement of inhibition or activation of a standard marker produced in the cell is determined. Cells can be either isolated from an animal, including a transformed cultured cell, or can be in a living animal. Such assays are also known to one of ordinary skill in the art.

Assays to detect and/or quantitate the ability of the compound to bind to a target can include labelling the compound, incubating the target with the compound, and determining binding by detecting the label bound to the target. Competition experiments, in which the compound is incubated with the target in the presence of labelled inhibitors, can also be performed.

In instances where the target macromolecule is a protein kinase, assays to determine activity include any assay wherein a nucleoside or nucleotide are cofactors or substrates of the peptide of interest, and particularly any assay involving phosphotransfer in which the substrates and or cofactors are ATP, GTP, Mg, Mn, peptides or polymeric amino acids. The assay can be an enzyme inhibition assay, utilizing a full length or truncated kinase, said enzyme having sequence homology with that of mammalian origin, including for example, human, murine, rat, and the like. The enzyme is contacted with the compound and a measurement of the binding affinity of the compound against a standard is determined. Such assays are known to one of ordinary skill in the art.

Advantages of the Invention

Ligand breeding serves as a rapid method of ligand design and also serves as a tool for finding appropriate sidechain exchanges between different scaffolds. The automated methods described here can increase the speed of ligand design by orders of magnitude when compared to other available de novo design programs. Molecular ligand breeding also explicitly takes advantage of known structural information on ligand-target macromolecule interactions. The new output ligands not only contain structural elements known to bind to the relevant target, but the structural elements are combined strictly to ensure that they all bind in the same position and orientation as in other known ligands of that target macromolecule, or homologs thereof. Implementation of the methods with a specified subset of structures, e.g., structures identified on the basis of various user-specified criteria for homology, further improves the potential of the output ligands. All of these features enhance the likelihood that the new output ligands will bind to the target. The continuing development of high-quality docking functions will increase the number of chemical structures to which these methods can be applied.

Molecular ligand breeding can also provide a means of determining positions on different scaffolds at which structural elements may be interchanged. Such a pair of sites for exchange represents not just an opportunity to swap the individual structural elements from the starting structures, but a likely point from which structural elements in general will be interchangeable. And it is likely that not only the structural elements, but also the entire SAR (structure-activity relationship) from such sites will be transferable. This recognition of equivalent sites on different scaffolds makes new information available, even before new molecules are made. This transfer of SAR does require that additivity in binding applies, and while there are cases of non-additivity in binding, they are the exception rather than the rule.

The methods described herein help predict which structural elements might be exchanged and which sidechain swaps will be tolerated. Even among sidechains binding in the same pocket of the active site, the different angles of approach to that pocket will lead to different sets of acceptable structural elements on different scaffolds. The methods described herein, in which spatial arrangements of atoms and bonds are electronically read and manipulated, facilitate determination of which sidechains are appropriate. Thus, the automated iterative embodiments delineated herein avoid human bias (i.e., of the scientist) that might inadvertently lead one to overlook a particular ligand or combination having a particular biological activity against a target, e.g., a potential inhibitor, antagonist, or agonist.

The ligand breeding methods can also be used in late stages of drug design in which initial leads have proven unsuitable (due to insolubility, poor cell permeability, metabolic instability, toxicity, etc.). Other situations in which the present methods would be useful include those in which large amounts of structural data are available, as is the case for gene family based inhibitor design.

The automation of the practice of swapping fragments between different ligands of a given target has been shown to reproduce the inhibitors generated by hand for HIV-1 protease and protein kinases (see Examples below). The compounds produced by these ligand recombinations include examples of both new scaffolds and substituent exchanges between scaffolds. The automation of the method also allows it to be performed recursively, such that the compounds produced by molecular ligand breeding can be passed through the process again, recombining with each other to generate still more new compounds. In one aspect, the reiterative process of ligand generation can be automated to run to exhaustion, that is, repeated separation and recombination of molecule fragments (i.e., halves) until no new ligands result relative to those created in that particular ligand breeding session. In this way it is possible to generate results in which a new linker is introduced between two important binding elements. The method can also be applied in situations where less structural information is available. High-quality docked structures may be combined with experimentally determined structures for processing, or inhibitors of structurally related targets can be used as input to molecular ligand breeding. This latter application is likely to become more prevalent as gene-family based drug discovery programs proliferate.

EXAMPLES

Example 1

HIV-1 Aspartyl Protease Ligands

HIV-1 aspartyl protease is an enzyme vital to the replication of the human immunodeficiency virus (HIV). This target has a large number and variety of potent inhibitors and publicly available crystal structures.

All backbone atoms of the HIV-1 protease were used to overlay the protein structures on to PDB entry 1HSH. Once the set of structures was aligned and the ligands were in a common reference frame, the ligands were saved to an SD file without explicit hydrogen atoms. The Python script breed.py, implemented with the OEChem library for small molecule processing, was then used to process this file in the following manner. Each pair of ligands was considered in turn to find all matching bonds between the two molecules. Bonds were considered matching if: they were of the same order, the atoms at each end of the bond must be within one angstrom of each other, and the angle between the bond vectors of the two bonds were no greater than 15°.

Figure 6:
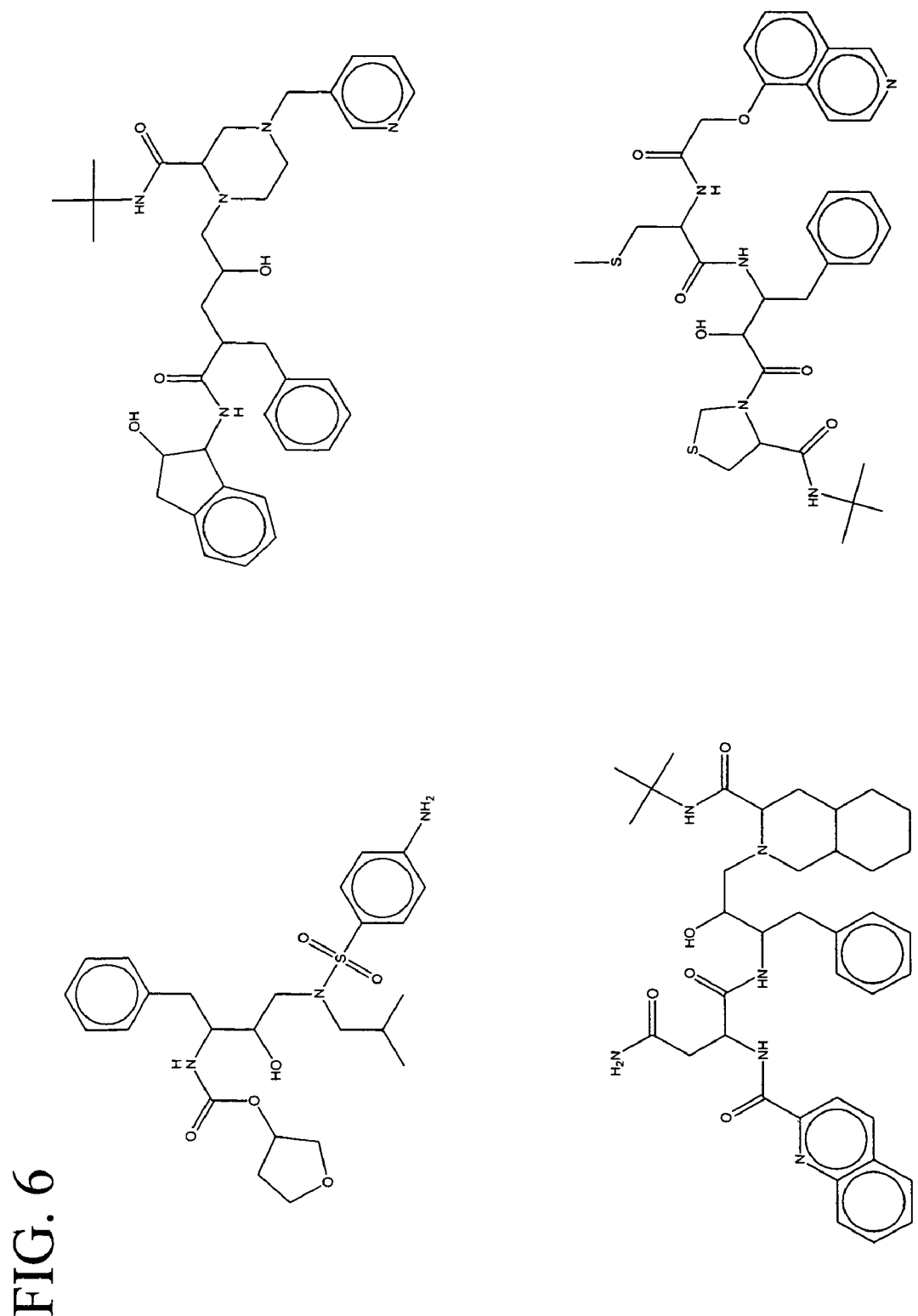
FIG. 6 is a diagram depicting the structures of four HIV protease inhibitors used as initial ligands for ligand breeding.

For the HIV-1 protease inhibitors, four compounds were initially selected for molecular ligand breeding (FIG. 6). These ligands came from the PDB crystal structures 1HPV, 1HSG, 1HPX, and 1HXB. The sets were chosen to ensure that each compound shared at least one matching bond with another molecule in the set. The small sets allowed manual inspection of the results to verify that they are both correct (that no errors were made in the splitting or recombining of molecules) and complete (that recombination was executed at all matching bonds).

Figure 7:
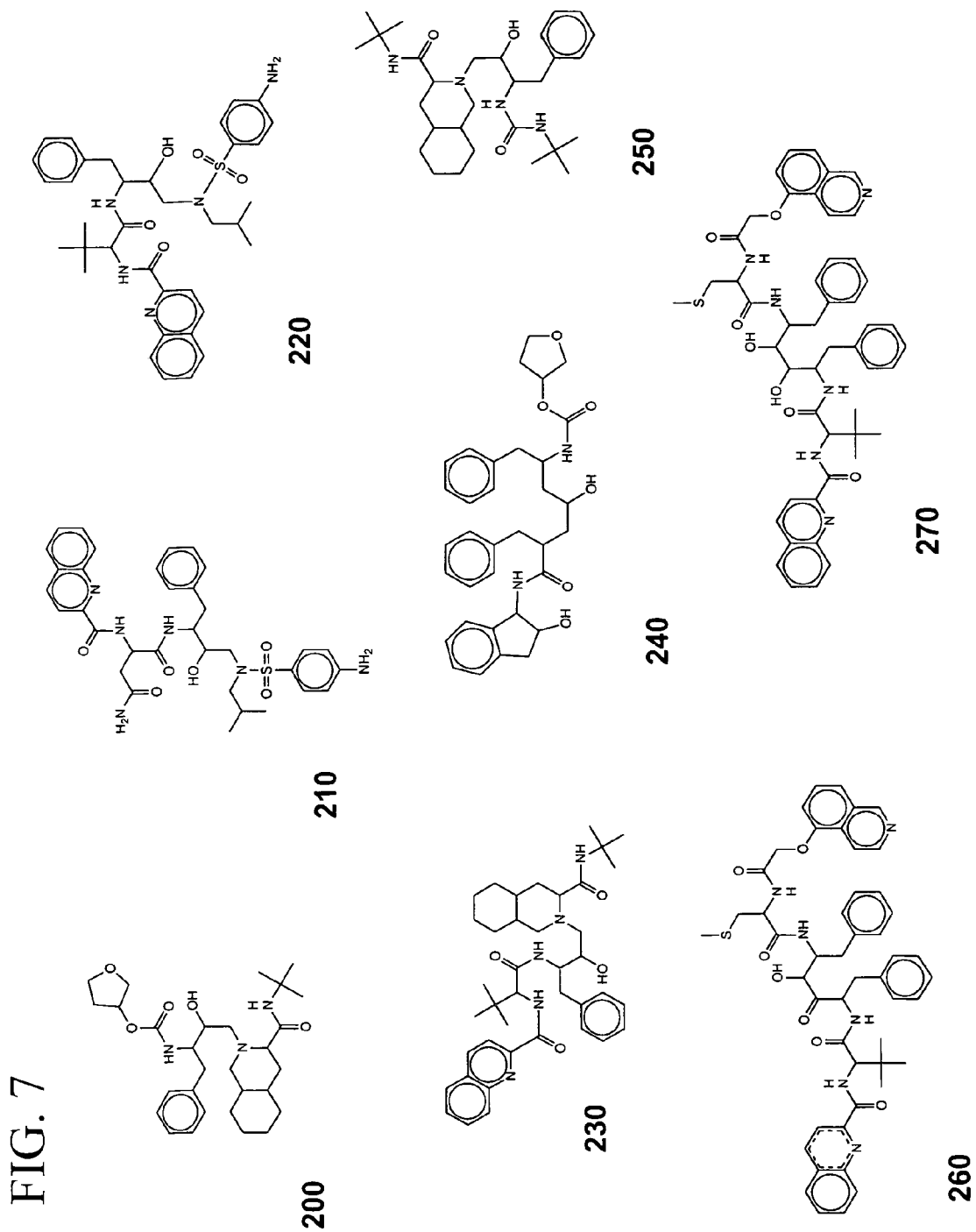
FIG. 7 is a diagram depicting the structures of eight ligands produced from one and two cylces of ligand breeding with the HIV protease inhibitors depicted in FIG. 6.

The four original HIV-1 protease inhibitors served as a first test of molecular ligand breeding since they were all derived from the same target. Passing these four compounds through BREEDER generated 20 new compounds. A second round of processing led to an additional 81 compounds, for a total of 101 new potential inhibitors. The generation of 101 new compounds (82 of which contain a hydroxyl group known to be critical for interactions with the target protein) by molecular ligand breeding from the four initial inhibitors indicates that the method is effective. FIG. 7 depicts a subset of structures generated by the breeding process with the HIV protease inhibitors. Structures 200, 210, and 230 were produced after one cycles of breeding. Structures 220, 240, 250, 260, and 270 were produced after two cycles of breeding.

In addition to the exchange of substituents at several active site pockets, the new compounds include numerous examples of novel peptidomimetic backbones not present in the original compounds. Appropriate exchanges of backbone fragments generally do require accurate structural information and considerable care in modeling to be performed successfully. The ligand breeding procedure is particularly useful in this capacity. It should be noted that some of the novel backbones generated lack the hydroxyl group known to be important for binding between Asp sidechains 25 and 125 of the protease. Nevertheless, these (19 out of 101) compounds can be easily filtered out leaving numerous novel, potentially potent inhibitor scaffolds.

To address the possibility that these four compounds might have represented a special case since they were chosen specifically for their potential for fragment recombination, and demonstrate the capability of this method for HIV-1 protease inhibitors in general, six additional compounds were added to the initial four, and the process was repeated. The additional six ligands come from the PDB crystal structures 1B6J, 1B6K, 1HII, 1IIQ, 1OHR, and 4PHV. As a group, these represent a diverse set of ten inhibitors, to verify that molecular ligand breeding can generate new inhibitors from a larger set of arbitrarily selected ligands.

In this case, 75 new structures were generated in the first round of breeding, and 716 compounds were generated in the second round. Among these 791 compounds, 767 contain the Asp-bridging hydroxyl.

Example 2

Kinase Ligands

Protein kinases are the enzymes responsible for the transfer of the gamma phosphate of ATP to the hydroxyl side chains of substrate proteins. These enzymes are of interest to biologists due to their critical role in many biological processes. Ligand breeding was performed with a set of known kinase inhibitors.

Figure 8:
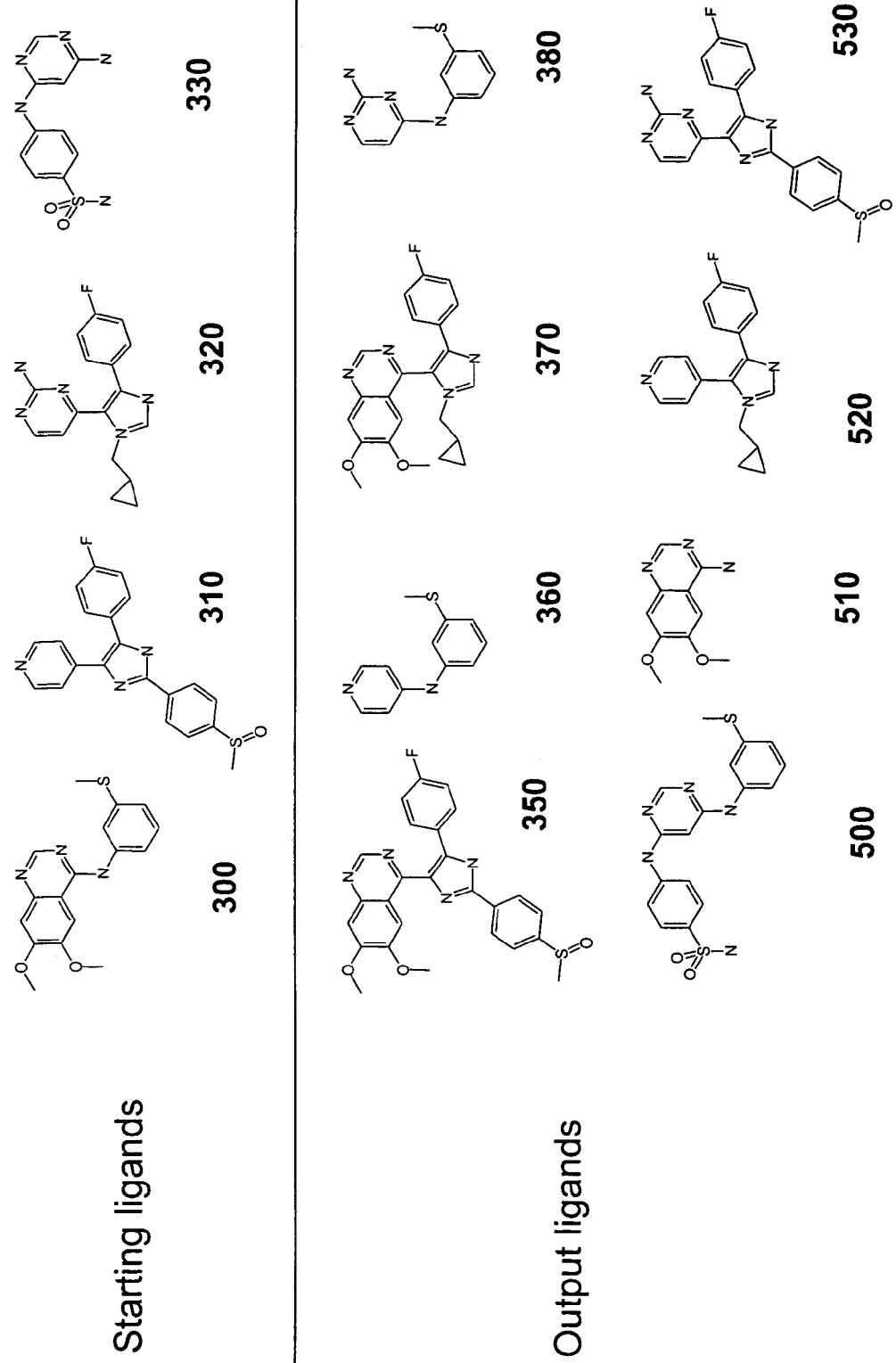
FIG. 8 is a diagram depicting structures of two ligands of p38 MAP kinase (310 and 320) and two ligands of cyclin-dependent kinase-2 (300 and 330) used as initial ligands for ligand breeding (top row), and output ligands produced by one cycle of ligand breeding using these initial structures (second and third rows).

The first four kinase ligands, shown at the top of FIG. 8, come from the p38 MAP kinase (p38) (310 and 320) and cyclin-dependent kinase 2 (CDK2) (300 and 330) crystal structures with PDB codes 1A9U, 1BMK, 1D19 and 1JSV. A sampling of 8 compounds produced by ligand breeding is shown in the second and third rows. To perform ligand breeding, the hinge region of each kinase was superimposed with residues 145-149 of the hinge region of c-Jun N-terminal kinase 3 (JNK3). The hinge region was chosen due to its conservation between kinases.

One ligand 520 generated by the process, is a known 160 nM inhibitor of p38. As a crystal structure is available for this compound (PDB code 1BL6) a comparison could be made between the molecular ligand breeding "docked" structure and the experimentally determined structure. Superpositioning was performed by overlaying the protein of 1BL6 with the JNK3 structure used for molecular ligand breeding of all kinase structures. The rms deviation in atom position between the two molecules is 1.07 Å, which is small, given the method of superposition. Thus the method predicted a known kinase inhibitor and gave its binding orientation with a high degree of accuracy. It seems extremely likely that ligand 530 may also be a potent inhibitor of p38, given that ligands 300, 310, and 320 are all inhibitors, and visual inspection suggests that all of the same key interactions will be made by 530. Several of the other compounds in FIG. 8 may function as kinase inhibitors. All of them are composites of known kinase inhibitors, with hydrogen bonding functionality at the ATP site hinge, reasonable binding conformations, and hydrophobic functionality that fits well within the ATP site. 4-amino quinazolines such as 510 are also known to be inhibitors of numerous kinases such as c-KIT, FLT-3 and epithelial growth factor receptor, so this compound may inhibit kinases. Not all of the molecular ligand breeding results from FIG. 8 are known kinase inhibitors. The compounds 350, 360, and 370 may be novel.

All references cited herein, whether in print, electronic, computer readable storage media or other form, are expressly incorporated by reference in their entirety, including but not limited to, abstracts, articles, journals, publications, texts, treatises, internet web sites, databases, software packages, patents, and patent publications. A number of embodiments of the invention have been described. Nevertheless, it will be understood that various modifications may be made without departing from the spirit and scope of the invention. Accordingly, other embodiments are within the scope of the following claims.

What is claimed is:

1. A method of identifying potential ligands for protein targets comprising:
   (1) providing a set of models, wherein each model comprises three-dimensional structural information for a ligand or a ligand: protein complex, wherein each ligand comprises a plurality of atoms and a plurality of bonds, wherein each model is related to the other models of the set by 25% or more sequence homology for proteins, or by; a structural homology between the ligands of at least 4-6 atoms in common; and
   wherein the structural information is derived from physical observation and/or computational inference;
   (2) mapping spatial relationships between the models such that the models are superimposed with respect to the homologous structural feature;
   (3) identifying one or more pairs of matching bonds between ligands of the set, wherein the matching bonds comprise a bond of a first ligand (B1) and a bond of a second ligand (B2) that are superimposed in step (2) such that
      (i) an atom at each end of the bond (B1) is within 1.8 angstrom of an atom at each end of the bond (B2),
      (ii) the bond (B1) and the corresponding bond (B2) are of the same bond order, and
      (iii) the bond (B1) and the corresponding bond (B2) are related by an angle of 30° or less;
   (4) selecting a plurality of subsets of atoms and/or bonds from each ligand;

wherein each subset comprises a bond and/or, an atom connected to the matching bond as identified in (3);

(5) generating and displaying output ligands, each output ligand comprising atoms and/or bonds of a first subset as selected in (4) and atoms and/or bonds of a second subset as selected in (4), wherein the first subset and the second subset comprise atoms and/or bonds derived from opposite ends of a matching bond as selected in (4) wherein steps (1) through (5) are performed by a suitably programmed computer.

2. The method of claim 1, wherein the output ligands comprise all atoms represented in the ligands of step (1).

3. The method of claim 1, wherein each model of the set comprises a ligand:protein complex.

4. The method of claim 3, wherein each model of the set comprises an identical protein.

5. The method of claim 3, wherein the structural information comprises information derived by a computational inference.

6. The method of claim 1, wherein one or more models of the set consist of a ligand.

7. The method of claim 1, wherein the protein is a protein kinase, a G-protein coupled receptor, an immunoglobulin superfamily protein, a protease, or a zinc-finger containing protein.

8. The method of claim 1, wherein the structural information is derived from a physical observation.

9. The method of claim 1, wherein at least one ligand of (1) is a small molecule.

10. The method of claim 1, wherein the ligands are less than 1000 atomic mass units (a.m.u.).

11. The method of claim 1, wherein the ligands are less than 600 a.m.u.

12. The method of claim 1, wherein the structural homology comprises homology between a framework of the ligands.

13. The method of claim 1, wherein the structural homology comprises homology between a pharmacophore model of the ligands.

14. The method of claim 1, wherein the sequence homology for proteins is at least 40%.

15. The method of claim 14, wherein the structural information comprises a shared polypeptide fold.

16. The method of claim 1, wherein the set comprises at least three models.

17. The method of claim 1, further comprising the steps of:
(6) comparing output ligands of step (5) to the ligands of step (1); and
(7) storing output ligands that are not identical to the ligands used in a previous iteration of steps (2)-(5) in a machine-readable medium.

18. The method of claim 17, further comprising generating one or more output models, wherein each output model comprises the stored ligand docked into a target macromolecule.

19. The method of claim 18, further comprising refining the output models.

20. The method of claim 19, wherein the refining comprises performing energy minimization computations.

21. The method of claim 20, further comprising evaluating the output models.

22. The method of claim 21, further comprising assigning a score to each output model based on the evaluating.

23. The method of claim 22, further comprising obtaining a composition comprising a compound including a ligand from a subset of output models, wherein the subset comprises output models having a score in a preselected range.

24. The method of claim 23, further comprising evaluating the composition.

25. The method of claim 24, wherein the evaluating comprises determining the ability of the compound to bind a target protein or the ability of the compound to modulate activity of a target protein.

26. The method of claim 17, wherein steps 2-7 are repeated, and wherein the models superimposed in step (2) comprise the stored output ligands of step (7).

27. The method of claim 26, wherein the repeating is automatic.

28. The method of claim 27, wherein the repeating stops when each ligand of step (7) is identical to a ligand mapped in the previous step (2) of the repetition.

29. The method of claim 1, wherein the structural information comprises hydrogen atoms of the ligands and the bonds to hydrogen atoms.

30. The method of claim 1, wherein the structural information does not comprise hydrogen atoms of the ligands.

31. The method of claim 1, wherein the ligands comprise a macrocyclic moiety, and wherein at least two matching bonds between the ligands are identified within the macrocycle of each ligand.

32. A method of identifying potential ligands for a protein comprising:
(1) selecting a set of models from a plurality of models, wherein the selecting comprises identifying models comprising 25% or greater sequence homology for proteins or a structural homology between the ligands of at least 4-6 atoms in common, wherein each model comprises three-dimensional structural information for a ligand:protein complex, wherein each ligand comprises a plurality of atoms and a plurality of bonds; and
wherein the structural information is derived from physical observation and/or computational inference;
(2) providing the set of models;
(3) mapping spatial relationships between the models such that the models are superimposed with respect to the homologous structural feature;
(4) identifying one or more pairs of matching bonds between ligands of the set, wherein the matching bonds comprise a bond of a first ligand (B1) and a bond of a second ligand (B2) that are superimposed in step (2) such that
(i) an atom at each end of the bond (B1) is within 1.8 angstrom of an atom at each end of the bond (B2),
(ii) the bond (B1) and the corresponding bond (B2) are of the same bond order, and
(iii) the bond (B1) and the corresponding bond (B2) are related by an angle of 30° or less;
(5) selecting a plurality of subsets of atoms and/or bonds from each ligand;
wherein each subset comprises a bond and/or, an atom connected to a matching bond as identified in (4);
(6) generating and displaying output ligands, each output ligand comprising atoms and/or bonds of a first subset as selected in (5) and atoms and/or bonds of a second subset as selected in (5), wherein the first subset and the second subset comprise atoms and/or bonds derived from opposite ends of a matching bond as selected in (5) wherein steps (1) through (6) are performed by a suitably programmed computer.

33. An apparatus comprising:
(a) a memory that stores executable instructions; and
(b) a processor that executes the instructions to:
(1) provide a set of models, wherein each model comprises three-dimensional structural information for a ligand or a ligand:protein complex, wherein each ligand comprises a plurality of atoms and a plurality of bonds, and wherein each model is related to the other models of the set by 25% or more sequence homology for proteins, or by a structural homology between the ligands of at least 4-6 atoms in common; and wherein the structural information is derived from physical observation and/or computational inference;

(2) map spatial relationships between the models such that the models are superimposed with respect to the homologous structural feature;

(3) identify one or more pairs of matching bonds between ligands of the set, wherein the matching bonds comprise a bond of a first ligand (B1) and a bond of a second ligand (B2) that are superimposed in step (2) such that (i) an atom at each end of the bond (B1) is within 1.8 angstrom of an atom at each end of the bond (B2), (ii) the bond (B1) and the corresponding bond (B2) are of the same bond order, and (iii) the bond (B1) and the corresponding bond (B2) are related by an angle of 30° or less;

(4) select a plurality of subsets of atoms and/or bonds from each ligand;

wherein each subset comprises a bond and/or, an atom connected to the matching bond as identified in (3);

(5) generate output ligands, each output ligand comprising atoms and/or bonds of a first subset as selected in (4) and atoms and/or bonds of a second subset as selected in (4), wherein the first subset and the second subset comprise atoms and/or bonds derived from opposite ends of a matching bond as selected in (4);

(6) compare output ligands to the ligands of step (1);

(7) store output ligands that are not identical to the ligands of step (1);

(8) repeat steps (2)-(7), wherein the models superimposed in step (2) comprise the stored output ligands of step (7);

wherein the repeating stops when each output ligand of step (7) is identical to a ligand provided in the previous step (2) of the repetition.

34. An article comprising machine-readable media that stores executable instructions, the instructions causing a machine to:

(1) provide a set of models, wherein each model comprises three-dimensional structural information for a ligand or a ligand:protein complex, wherein each ligand comprises a plurality of atoms and a plurality of bonds;

wherein each model is related to the other models of the set by 25% or more sequence homology for proteins, or by a structural homology between the ligands of at least 4-6 atoms in common; and wherein the structural information is derived from physical observation and/or computational inference;

(2) map spatial relationships between the models such that the models are superimposed with respect to the homologous structural feature;

(3) identify one or more pairs of matching bonds between ligands of the set, wherein the matching bonds comprise a bond of a first ligand (B1) and a bond of a second ligand (B2) that are superimposed in step (2) such that (i) an atom at each end of the bond (B1) is within 1.8 angstrom of an atom at each end of the bond (B2), (ii) the bond (B1) and the corresponding bond (B2) are of the same bond order, and (iii) the bond (B1) and the corresponding bond (B2) are related by an angle of 30° or less;

(4) select a plurality of subsets of atoms and/or bonds from each ligand;

wherein each subset comprises a bond and/or, an atom connected to the matching bond as identified in (3);

(5) generate and display output ligands, each output ligand comprising atoms and/or bonds of a first subset as selected in (4) and atoms and/or bonds of a second subset as selected in (4), wherein the first subset and the second subset comprise atoms and/or bonds derived from opposite ends of the matching bond as selected in(4);

(6) compare output ligands to the ligands of step (1);

(7) store output ligands that are not identical to the ligands of step (1);

(8) repeat steps (2)-(7), wherein the models superimposed in step (2) comprise the stored output ligands of step (7);

wherein the repeating stops when each output ligand of step (7) is identical to a ligand provided in the previous step (2) of the repetition.

35. An article comprising machine-readable media that stores executable instructions, the instructions causing a machine to:

(1) map spatial relationships between two or more models of ligands of a set such that the models are superimposed, wherein each ligand comprises a plurality of atoms and a plurality of bonds, and wherein each model comprises three-dimensional structural information for a ligand; and wherein the structural information is derived from physical observation and/or computational inference;

(2) identify one or more pairs of matching bonds between ligands of the set, wherein the matching bonds comprise a bond of a first ligand (B1) and a bond of a second ligand (B2) that are superimposed in step (2) such that (i) an atom at each end of the bond (B1) is within 1.8 angstrom of an atom at each end of the bond (B2), (ii) the bond (B1) and the corresponding bond (B2) are of the same bond order, and (iii) the bond (B1) and the corresponding bond (B2) are related by an angle of 30° or less;

(3) select a plurality of subsets of atoms and/or bonds from each ligand;

wherein each subset comprises a bond and/or, an atom connected to a matching bond as identified in (2);

(4) generate and display output ligands, each output ligand comprising atoms and/or bonds of a first subset as selected in (3) and atoms and/or bonds of a second subset as selected in (3), wherein the first subset and the second subset comprise atoms and/or bonds derived from opposite ends of the matching bond as selected in(3).

36. The method of any one of claims 1, 32, and 33 to 35, wherein the structural information derived from physical observation is derived from X-ray crystallography or NMR.

37. The method of any one of claims 1, 32, and 33 to 35, wherein the structural information derived from computational inference is derived by modeling the structure of a ligand in a target protein using computational means.

* * * * *